United States Patent
Fu et al.

(10) Patent No.: US 11,052,100 B2
(45) Date of Patent: Jul. 6, 2021

(54) STABLE NICOTINAMIDE RIBOSIDE COMPOSITION AND PREPARATION METHOD THEREOF

(71) Applicants: BONTAC BIO-ENGINEERING (SHENZHEN) CO., LTD, Guangdong (CN); Bontac InvitroLife Bio-technology (Shenzhen) Co., Ltd, Guangdong (CN); JIANGXI BONZYMES BIOTECHNOLOGY CO., LTD., Jiangxi (CN)

(72) Inventors: Rongzhao Fu, Guangdong (CN); Zhenwei Li, Guangdong (CN); Xinglin Guo, Guangdong (CN)

(73) Assignees: BONTAC BIO-ENGINEERING (SHENZHEN) CO., LTD, Guangdong (CN); BONTAC INVITROLIFE BIO-TECHNOLOGY (SHENZHEN) CO., LTD, Guangdong (CN); JIANGXI BONZYMES BIOTECHNOLOGY CO., LTD., Jiangxi (CN)

( * ) Notice: Subject to any disclaimer, the term of this patent is extended or adjusted under 35 U.S.C. 154(b) by 0 days.

(21) Appl. No.: 16/609,168

(22) PCT Filed: Aug. 17, 2018

(86) PCT No.: PCT/CN2018/101175
§ 371 (c)(1),
(2) Date: Oct. 28, 2019

(87) PCT Pub. No.: WO2019/210607
PCT Pub. Date: Nov. 7, 2019

(65) Prior Publication Data
US 2020/0323891 A1    Oct. 15, 2020

(51) Int. Cl.
A61K 31/706 (2006.01)
A61P 17/10 (2006.01)
A61K 47/26 (2006.01)

(52) U.S. Cl.
CPC ............ *A61K 31/706* (2013.01); *A61K 47/26* (2013.01); *A61P 17/10* (2018.01)

(58) Field of Classification Search
None
See application file for complete search history.

(56) References Cited

U.S. PATENT DOCUMENTS

| 2013/0165398 A1* | 6/2013 | Huber | A23L 2/39 514/43 |
| 2016/0374908 A1* | 12/2016 | Hakozaki | A61K 8/0283 424/401 |
| 2018/0134743 A1* | 5/2018 | Migaud | C07D 307/20 |

FOREIGN PATENT DOCUMENTS

CN    106955290 A    7/2017

OTHER PUBLICATIONS

Wu, Meng et al.; "Nicotinamide Riboside Attenuates Injury of Mouse Diabetic Cardiomyopathy and Possible Mechanism"; Progress in Modern Biomedicine, vol. 18, Issue No. 3, Feb. 2018, pp. 423-427.

* cited by examiner

*Primary Examiner* — Dale R Miller
(74) *Attorney, Agent, or Firm* — Muncy, Geissler, Olds & Lowe, P.C.

(57) ABSTRACT

A nicotinamide riboside composition and preparation method thereof, the icotinamide riboside composition comprises nicotinamide riboside and/or a salt thereof and konjac glucomannan or rebaudioside A. The nicotinamide riboside composition provided by the present invention, used to increase the concentration of NAD in cells, thereby preventing and improving various unhealthy conditions caused by NAD deficiency. is stable in property and easy to store and transport.

9 Claims, No Drawings

STABLE NICOTINAMIDE RIBOSIDE COMPOSITION AND PREPARATION METHOD THEREOF

CROSS-REFERENCE TO RELATED APPLICATIONS

This application is the national stage of International Application No. PCT/CN2018/101175 filed Aug. 17, 2018, the entire contents of which are incorporated herein by reference.

TECHNICAL FIELD

The present invention relates to the technical field of biomedicine, and in particular, to a stable nicotinamide riboside composition and a preparation method thereof.

RELATED ART

Nicotinamide riboside (NR) is also known as nicotinamide nucleoside, nicotinamide ribonucleoside, nicotinic ribose/nucleoside, nicotinic nucleoside, and β-D-nicotinamide nucleoside. The CAS number is 1341-23-7. The structural form thereof is shown below.

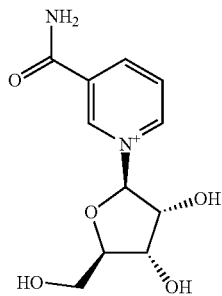 [SMILES: NC(=O)c1ccc[n+]([C@@H]2O[C@H](CO)[C@@H](O)[C@H]2O)c1]

Nicotinamide riboside is a precursor of nicotinamide adenine dinucleotide (NAD) and represents a source of vitamin B3. Studies have shown that supplementation with nicotinamide riboside can increase the concentration of NAD in cells, thereby preventing and improving various unhealthy conditions caused by NAD deficiency.

However, nicotinamide riboside contains high energy glucosidic bonds which are spontaneously unstable in an aqueous environment and decompose into nicotinamide and riboside products. The spontaneous decomposition occurs for hours or days depending on specific environmental conditions, making it difficult to maintain any nicotinamide riboside naturally existing in food. Therefore, it is almost impossible to supplement nicotinamide riboside by food.

At present, humans have made great progress in the artificial preparation of nicotinamide riboside, which can produce a relatively pure product of nicotinamide riboside at a lower cost. However, because nicotinamide riboside is highly hygroscopic, a monomer becomes a sticky solid at ambient temperature and humidity within seconds or minutes and disintegrates into oil within hours. In order to maintain nicotinamide riboside as a dry solid, nicotinamide riboside needs to be stored in an absolutely dry environment, or needs to be frozen and stored at about −20° C., which seriously restricts the commercial application and promotion of nicotinamide riboside. Therefore, the development of stable nicotinamide riboside products has become a major problem that badly needs to be solved in front of people.

SUMMARY

In order to solve the technical problem mentioned in Related Art that a nicotinamide riboside monomer cannot be preserved, promoted and applied due to moisture absorption and decomposition, the present invention is directed to a nicotinamide riboside composition which is stable in property and easy to store, transport and use.

In order to achieve the above object, the inventors have, after extensive experimentation, finally developed a stable nicotinamide riboside composition. The composition comprises nicotinamide riboside and/or a salt thereof and konjac glucomannan or rebaudioside A.

Specifically, the stable nicotinamide riboside composition of the present invention is in any one of the following forms: consisting of nicotinamide riboside and konjac glucomannan; consisting of nicotinamide riboside and rebaudioside A; consisting of nicotinamide riboside, konjac glucomannan, and other pharmaceutically acceptable ingredients; consisting of nicotinamide riboside, rebaudioside A, and other pharmaceutically acceptable ingredients; consisting of nicotinamide riboside salt and konjac glucomannan; consisting of nicotinamide riboside salt and rebaudioside A; consisting of nicotinamide riboside salt, konjac glucomannan, and other pharmaceutically acceptable ingredients; consisting of nicotinamide riboside salt, rebaudioside A, and other pharmaceutically acceptable ingredients; consisting of nicotinamide riboside, nicotinamide riboside salt, and konjac glucomannan; consisting of nicotinamide riboside, nicotinamide riboside salt, and rebaudioside A; consisting of nicotinamide riboside, nicotinamide riboside salt, konjac glucomannan, and other pharmaceutically acceptable ingredients; or, consisting of nicotinamide riboside, nicotinamide riboside salt, rebaudioside A, and other pharmaceutically acceptable ingredients. The nicotinamide riboside, the nicotinamide riboside salt, the konjac glucomannan, and the rebaudioside A in the foregoing compositions of various forms are 100% pure monomers or non-100% pure monomers containing appropriate amounts of impurities.

The nicotinamide riboside salt is one or more salt forms selected from the group consisting of fluorides, chlorides, bromides, iodides, formates, acetates, ascorbates, benzoates, carbonates, citrates, carbamates, formates, gluconates, lactates, methyl bromides, methyl sulfates, nitrates, phosphates, diphosphates, succinates, sulfates, and trifluoroacetates.

Preferably, the nicotinamide riboside salt is a nicotinamide riboside chloride. The molecular formula thereof is C11H15N2O5•Cl. The structural formula is shown below.

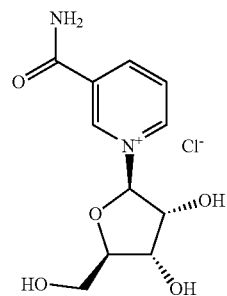 [SMILES: NC(=O)c1ccc[n+]([C@@H]2O[C@H](CO)[C@@H](O)[C@H]2O)c1 ; [Cl-]]

Konjac glucomannan, also known as glucomannan, or KGM for short, is a medium-sized nonionic linear polysaccharide contained in konjac tubers. It is formed by the combination of glucose and mannose with β-1,4 glucosidic bonds. It is a natural polymer soluble dietary fiber, which is an excellent product in all dietary fibers, contains no calories, and is hydrophilic, gelatinous, cohesive, antibacterial, film-forming, edible, and characterized by satiety.

Rebaudioside A (RA) is a diterpene glycoside compound, which is the main active ingredient in the dried leaves of compositae *Stevia rebaudiana*. The sweetness is 300-400 times that of sucrose. RA is the best sweetener in stevia. But, the calorie is only 1/300 of that of sucrose. Thus, RA is an ideal sweetener that replaces sucrose and is the only "Generally Recognized as Safe" (GRAS) substance uniquely recognized by the FDA.

Compared to rebaudioside A, konjac glucomannan is a more preferred option of the present invention, which makes the composition of the present invention have higher stability and better product properties. Specifically, a nicotinamide riboside composition in the shape of an amorphous white powder having excellent fluidity is obtained by using konjac glucomannan. A nicotinamide riboside composition which is pale yellow to white and granulated to powder is obtained by using rebaudioside A.

Preferably, a weight ratio of the nicotinamide riboside and/or the salt thereof to the konjac glucomannan or the rebaudioside A in the composition is 1:1-2. If the amount of the konjac glucomannan or the rebaudioside A added is too small, the properties and stability of the composition product are affected, so that a stable white powder cannot be obtained. More preferably, a weight ratio of the nicotinamide riboside and/or the salt thereof to the konjac glucomannan or the rebaudioside A is 1:1.5-2.

Preferably, the composition is an amorphous powder. All the components of the composition are uniformly mixed.

Preferably, the weight percentage content of the nicotinamide riboside and/or the salt thereof in the composition is 10% or more.

The present invention also provides a preparation method of a stable nicotinamide riboside composition, which comprises: weighing nicotinamide riboside and/or a salt thereof and konjac glucomannan or rebaudioside A respectively, and uniformly mixing to obtain the composition. The foregoing nicotinamide riboside and/or salt thereof and konjac glucomannan or rebaudioside A are commercially available solid powders or are homemade solid powders. Compared to rebaudioside A, konjac glucomannan is a more preferred option of this method.

Preferably, in the above preparation method, a ratio of the nicotinamide riboside and/or the salt thereof to the konjac glucomannan or the rebaudioside A is a weight ratio of the nicotinamide riboside and/or the salt thereof to the konjac glucomannan or the rebaudioside A, which is equal to 1:1-2. If the amount of the konjac glucomannan or the rebaudioside A added is too small, the properties and stability of the composition product are affected, so that a stable white powder cannot be obtained. More preferably, the ratio of the nicotinamide riboside and/or the salt thereof to the konjac glucomannan or the rebaudioside A is 1:1.5-2.

The present invention also provides a second preparation method of a stable nicotinamide riboside composition, which comprises: taking an aqueous solution of nicotinamide riboside, adding a hydrochloric acid to adjust the pH value to 3-4, adding konjac glucomannan or rebaudioside A, performing full dissolution and uniform mixing, and freeze-drying to obtain the composition.

The aqueous solution of nicotinamide riboside is a solution obtained by dissolving a commercially available or homemade nicotinamide riboside solid powder in water, or is a solution obtained by enzymatically preparing an impurity-removed enzyme reaction solution obtained by nicotinamide riboside. The preparation of nicotinamide riboside by enzyme catalysis refers to the process of converting a specific substrate (precursor of nicotinamide riboside) into nicotinamide riboside under the catalysis of biological enzymes. For example, acid phosphatase catalyzes nicotinamide mononucleotide to be converted into nicotinamide riboside, etc. The impurity-removed enzyme reaction solution refers to that the solution mainly contains the product nicotinamide riboside, and contains no or a trace amount of other impurities such as a substrate, an enzyme, or an inorganic ion.

The above konjac glucomannan or rebaudioside A is commercially available solid powders or is homemade solid powders. Compared to rebaudioside A, konjac glucomannan is a more preferred option of this method.

Preferably, in the above second preparation method, the concentration of the aqueous solution of nicotinamide riboside is 40-90 g/L based on the nicotinamide riboside, preferably 50-60 g/L. Konjac glucomannan or rebaudioside A is added in 90 g/L of the aqueous solution of nicotinamide riboside. If the amount of the konjac glucomannan or the rebaudioside A added is too small, the properties and stability of the composition product are affected, so that a stable white powder cannot be obtained.

Preferably, in the above second preparation method, the sublimation temperature in the freeze-drying process is controlled to be 25° C. or lower, and the moisture content in the composition is reduced to 2% or less by drying.

The present invention also provides a method for improving the stability of nicotinamide riboside, which comprises: adding konjac glucomannan or rebaudioside A into nicotinamide riboside and/or a salt thereof, and allowing the nicotinamide riboside and/or the salt thereof to coexist with the konjac glucomannan or the rebaudioside A in a state of uniform mixing.

Preferably, the amount of the konjac glucomannan or the rebaudioside A added is 1-2 times of the weight of the nicotinamide riboside and/or the salt thereof, preferably 1.5 times. Compared to rebaudioside A, konjac glucomannan is a more preferred option of this method.

The present invention also provides a drug, a health care product or a skin care product, which comprises the above stable nicotinamide riboside composition.

Beneficial Effects:

Compared with the existing technology, the nicotinamide riboside composition provided by the present invention is stable in property and easy to store and transport. The focus index of the composition during the 6-month test period is not significantly changed as determined by an accelerated test. The preparation process is simple, the cost is low, and industrialized mass production is facilitated.

DETAILED DESCRIPTION

The present invention will be further described in detail below with reference to specific embodiments. The following embodiments are illustrative of the present invention. The present invention is not limited to the following embodiments. The embodiments in which specific conditions are not indicated are carried out according to conventional conditions or conditions recommended by manufacturers. Unless otherwise stated, the raw materials and other chemical reagents used in the embodiments of the present invention are commercially available.

Embodiment 1

Raw material: 50 g of nicotinamide riboside amorphous powder, 100 g of konjac glucomannan amorphous powder, and 100 g of rebaudioside A amorphous powder.

Preparation: The above raw materials nicotinamide riboside and konjac glucomannan or rebaudioside A were uniformly mixed to obtain the stable nicotinamide riboside composition of the present invention.

Embodiment 2

Raw material: 60 g of nicotinamide riboside chloride amorphous powder, 60 g of konjac glucomannan amorphous powder, and 60 g of rebaudioside A amorphous powder.

Preparation: The above raw materials nicotinamide riboside chloride and konjac glucomannan or rebaudioside A were uniformly mixed to obtain the stable nicotinamide riboside composition of the present invention.

Embodiment 3

Raw material: 50 g of nicotinamide riboside amorphous powder, 90 g of konjac glucomannan amorphous powder, and 90 g of rebaudioside A amorphous powder.

Preparation: The above nicotinamide riboside was dissolved in 1 L of water, a hydrochloric acid was added to adjust the pH value to 3-4, the above konjac glucomannan or rebaudioside A was added and stirred to be fully dissolved and uniformly mixed, a drying treatment was performed finally in a freeze-drying machine to control the sublimation temperature in the drying process to be below 25° C., and the stable nicotinamide riboside composition of the present invention was obtained.

Embodiment 4

Raw material: Enzymatic reaction solution obtained by enzymatically preparing nicotinamide riboside (catalysis through acid phosphatase (EC3.1.3.2) using nicotinamide mononucleotide (NMN) as a substrate), an appropriate amount of konjac glucomannan amorphous powder, and an appropriate amount of rebaudioside A amorphous powder.

Preparation: The above enzymatic reaction solution was purified to remove impurities to make the purity of nicotinamide riboside more than 90%, and then concentrated to make the concentration of nicotinamide riboside equal to 60 g/L, a hydrochloric acid was added to adjust the pH value to 3-4, konjac glucomannan or rebaudioside A was added to obtain a final concentration of 90 g/L and stirred to be fully dissolved and uniformly mixed, a drying treatment was performed finally in a freeze-drying machine to control the sublimation temperature in the drying process to be below 25° C., and the stable nicotinamide riboside composition of the present invention was obtained.

Embodiment 5

Stability Accelerated Test

The stability accelerated test was carried out on test subjects (nicotinamide riboside and the nicotinamide riboside composition prepared in Embodiment 1 to Embodiment 4 of the present invention) in accordance with the provisions of the Guidelines for Drug Stability Test in the Chinese Pharmacopoeia 2015. The test method was: taking 3 samples from each test subject in an environment with a temperature of 25° C.±2° C. and a relative humidity of 60% ±10%, taking samples once at the end of the $0^{th}$ month, $1^{st}$ month, $2^{nd}$ month, $3^{rd}$ month, and $6^{th}$ month during the test period, detecting the purity of nicotinamide riboside by HPLC, and calculating an average value of 3 parts. The test results are shown in Table 1. In the table, 1, 2, 3 and 4 in the first column represent Embodiment 1, Embodiment 2, Embodiment 3 and Embodiment 4, respectively, NR represents nicotinamide riboside, KGM represents konjac glucomannan, and RA represents rebaudioside A.

TABLE 1

| Test object | $0^{th}$ month | $1^{st}$ month | $2^{nd}$ month | $3^{rd}$ month | $6^{th}$ month |
|---|---|---|---|---|---|
| NR | 99.6% | 10.6% | 5.1% | 3.4% | 3.2% |
| 1-NR + KGM | 99.6% | 99.4% | 99.1% | 98.7% | 98.1% |
| 1-NR + RA | 99.6% | 99.3% | 98.8% | 98.3% | 97.9% |
| 2-NR + KGM | 99.3% | 99.2% | 99.2% | 98.9% | 98.3% |
| 2-NR + RA | 99.3% | 99.1% | 98.9% | 98.4% | 98.0% |
| 3-NR + KGM | 99.6% | 99.5% | 99.3% | 99.0% | 98.8% |
| 3-NR + RA | 99.6% | 99.3% | 99.0% | 98.7% | 98.5% |
| 4-NR + KGM | 99.7% | 99.8% | 99.5% | 99.2% | 98.9% |
| 4-NR + RA | 99.7% | 99.7% | 99.3% | 98.9% | 98.6% |

What is claimed is:

1. A stable nicotinamide riboside composition, comprising:
   nicotinamide riboside and/or a salt thereof; and
   konjac glucomannan,
   wherein a weight ratio of the nicotinamide riboside and/or the salt thereof to the konjac glucomannan in the composition is 1:1-2.

2. The stable nicotinamide riboside composition according to claim 1, wherein the nicotinamide riboside salt is a nicotinamide riboside chloride.

3. The stable nicotinamide riboside composition according to claim 1, being an amorphous powder.

4. The stable nicotinamide riboside composition according to claim 1, wherein the weight percentage content of the nicotinamide riboside and/or the salt thereof in the composition is 10% or more.

5. A method for improving the stability of nicotinamide riboside, comprising:
   adding konjac glucomannan or rebaudioside A into nicotinamide riboside and/or a salt thereof, and
   allowing the nicotinamide riboside and/or the salt thereof to coexist with the konjac glucomannan or the rebaudioside A in a state of uniform mixing.

6. The method for improving the stability of nicotinamide riboside according to claim 5, wherein an amount of the konjac glucomannan or the rebaudioside A added is 1-2 times of a weight of the nicotinamide riboside and/or the salt thereof.

7. A preparation method of a stable nicotinamide riboside composition, comprising:
   taking an aqueous solution of nicotinamide riboside;
   adding a hydrochloric acid to adjust the pH value to 3-4;
   adding konjac glucomannan or rebaudioside A;
   performing full dissolution and uniform mixing; and
   freeze-drying to obtain the composition, wherein a weight ratio of the nicotinamide riboside to the konjac glucomannan or the rebaudioside A in the composition is 1:1-2.

8. The preparation method of a stable nicotinamide riboside composition according to claim 7, wherein the aqueous solution of nicotinamide riboside is a solution obtained by enzymatically preparing an impurity-removed enzyme reaction solution obtained by nicotinamide riboside.

9. The preparation method of a stable nicotinamide riboside composition according to claim 7, wherein a concentration of the aqueous solution of nicotinamide riboside is 40-90 g/L based on the nicotinamide riboside, the konjac glucomannan or rebaudioside A is added in 90 g/L of the aqueous solution of nicotinamide riboside.

* * * * *